US00PP17182P3

(12) United States Plant Patent
Rubio

(10) Patent No.: US PP17,182 P3
(45) Date of Patent: Nov. 7, 2006

(54) PEACH TREE PLANT NAMED 'PLAWHITE 5'

(50) Latin Name: *Prunus persica*
Varietal Denomination: Plawhite 5

(75) Inventor: Ignacio Abascal Rubio, Navarra (ES)

(73) Assignee: Plantas De Navarra S.A., Navarra (ES)

( * ) Notice: Subject to any disclaimer, the term of this patent is extended or adjusted under 35 U.S.C. 154(b) by 248 days.

(21) Appl. No.: 10/678,900

(22) Filed: Oct. 2, 2003

(65) Prior Publication Data

US 2004/0117880 P1 Jun. 17, 2004

(51) Int. Cl.
*A01H 5/00* (2006.01)

(52) U.S. Cl. ..... Plt./195

(58) Field of Classification Search ..... Plt./195
See application file for complete search history.

*Primary Examiner*—Bruce R. Campell
*Assistant Examiner*—S. B. McCormick-Ewoldt
(74) *Attorney, Agent, or Firm*—Christie, Parker & Hale, LLP

(57) ABSTRACT

Described is a peach tree producing very early ripening fruit that has a low chilling requirement and bears clingstone fruit.

6 Drawing Sheets

Figure 1:
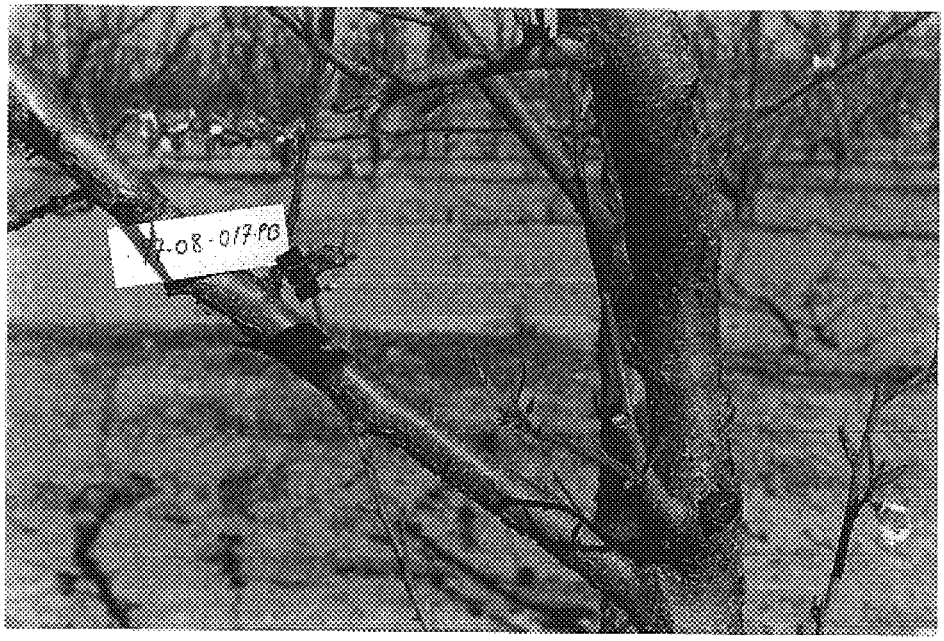

Classification: The present invention relates to a new variety of *Prunus persica* (L.) Bastch—Peach.

Variety denomination: The new plant has the varietal denomination of 'PLAWHITE 5'.

BACKGROUND OF THE INVENTION

The new variety of peach tree was created in a breeding program by crossing two parents; in particular, by crossing as seed parent a variety designated 88-023 (not patented) and as pollen parent a variety designated 89-027 (not patented). Both, female and male, are components of a parent collection made between plants issued from seeds obtained in a free pollination in a population of different origin. Both parental varieties are property and have not been commercialized or distributed.

The seeds resulting from this controlled hybridization were germinated in a greenhouse and planted in a field on the farm of La Mogalla in Cartaya (Huelva), Spain, 7° W., 37° N., 45 feet elevation. The seedlings subsequently fruited during and one, designated 97.08.017-PB, was selected for its very low chilling requirements (250 to 300 hours), its very early ripening, attractive fruit shape and color, white flesh, medium firm fruit, and good fruit quality. The original plant selection was propagated asexually, at the above noted location, by budding onto standard peach rootstock variety 'GF-677' and a test plot of four plants was established.

The new variety has been asexually multiplied several times at this location by budding onto 'GF-677' peach rootstock and no incompatibility with peach rootstock has occurred following budding. During all asexual multiplication, the characteristics of the original plant have been maintained and no aberrant phenotypes have appeared.

SUMMARY OF THE INVENTION

The 'PLAWHITE 5' Peach Tree is characterized as to novelty by producing fruit which have a very early season ripening date. In this regard, the present variety of peach tree needs a low chilling requirement (250 to 300 hours), bears clingstone fruit which are ripe for commercial harvesting and shipment during approximately April 15 to April 25 in the area grown. These harvesting dates are approximately 20 days earlier than the harvest dates of the commercial nectarine variety 'Earliglo' Nectarine Tree (U.S. Plant Pat. No. 7,402), and 30 days earlier than the harvest dates of the commercial peach variety 'Rich May' Peach Tree (U.S. Plant Pat. No. 7,432), and 50 days earlier than the harvest dates of the commercial peach variety 'Snow Brite' Peach Tree (U.S. Plant Pat. No. 8,195), and 65 days earlier than the harvest dates of the commercial nectarine variety 'Snow Queen' Nectarine Tree (notpatented). The present variety distinguishes itself from de 'Snow Brite' Peach Tree (U.S. Plant Pat. No. 8,195) by needing less hours chilling requirement (250 to 300 hours) than in 'Snow Brite' Peach Tree (U.S. Plant Pat. No. 8,195) are needed 900 to 1000 hours chilling requirement. The present variety distinguishes itself from de 'Snow Brite' Peach Tree (U.S. Plant Pat. No. 8,195) by producing smaller and slightly less firm fruits. The present variety distinguishes itself from the 'Earliglo' Nectarine Tree (U.S. Plant Pat. No. 7,402) by producing rounded-slightly flat shape fruit than in 'Earliglo' Nectarine Tree (U.S. Plant Pat. No. 7,402) is rounded shape, and the flesh color fruit in 'PLAWHITE 5' Peach Tree is white than in 'Earliglo' Nectarine Tree (U.S. Plant Pat. No. 7,402) is yellow. The present variety distinguishes itself from the 'Earliglo' Nectarine Tree (U.S. Plant Pat. No. 7,402), however, by producing smaller fruit size with approximately 80% to 85% of the fruit surface covered with a skin red color and the skin ground color is yellow-green than in 'Earliglo' Nectarine Tree (U.S. Plant Pat. No. 7,402) approximately 85-90% of the fruit surface is covered and the skin ground color is yellow-green. The present variety distinguishes itself from the 'Rich May' Peach Tree (U.S. Plant Pat. No. 7,432) by producing white flesh color fruits, and smaller fruit size, less firm fruits, and less surface colored fruits.

COMPARISON OF NEW VARIETY TO PARENTS:

Blooming time. The new variety has a blooming time considered very early in relation to other peach cultivars. Seed parent '88-027' (not patented) is considered early.

Harvest dates. 'Planjanomel' is ripe for commercial harvesting and shipment during approximately Apr. 15 to Apr. 25. These harvesting dates are approximately 30 days earlier than the harvest dates of the seed parent '88-023' and 15 days earlier than the harvest dates of the pollen parent '89-027'.

Fruit shape. 'PLAWHITE 5' distinguishes itself from its seed parent '88-023' by producing slightly flat gruit, while '88-023' produces fruit with a more rounded shape.

Fruit flesh color. 'Plajanomel' distinguishes itself from its pollen parent '89-027' by producing fruit with a white flesh color, while '89-027' produces fruit with a yellow flesh.

BRIEF DESCRIPTION OF THE ILLUSTRATIONS

The accompanying photographs show

Figure 2:
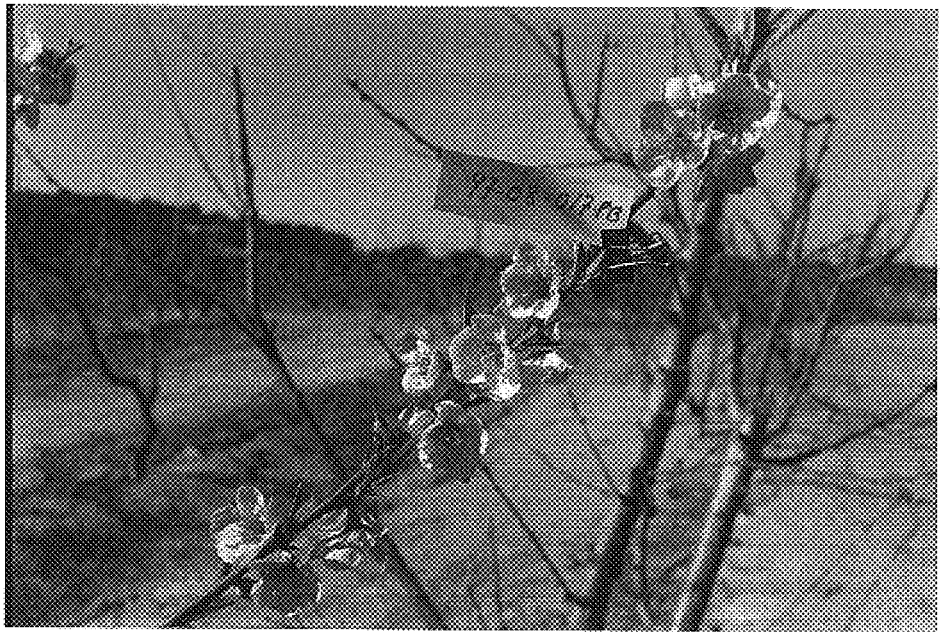
Figure 3:
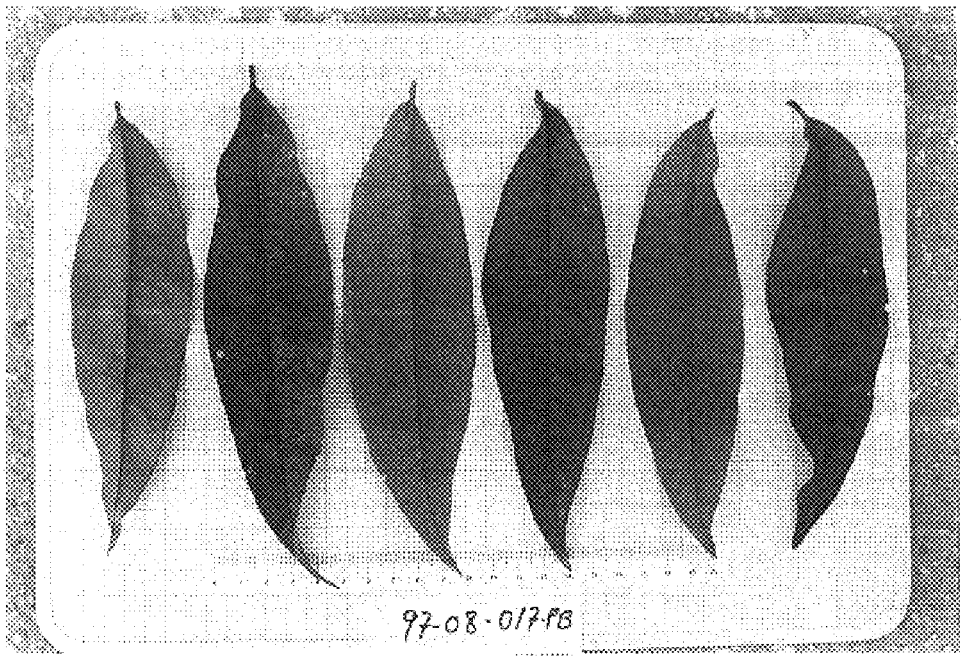
Figure 4:
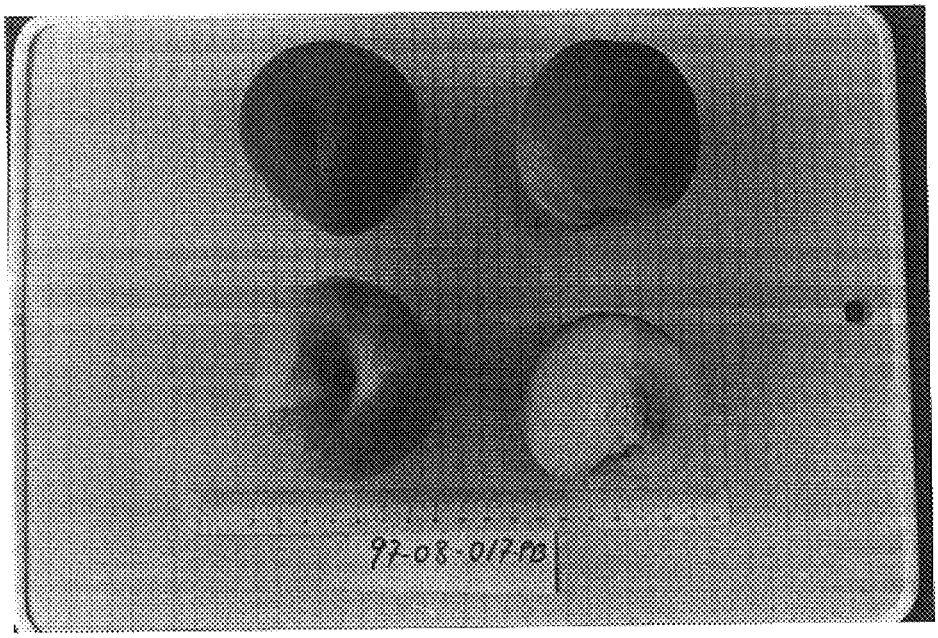
Figure 5:
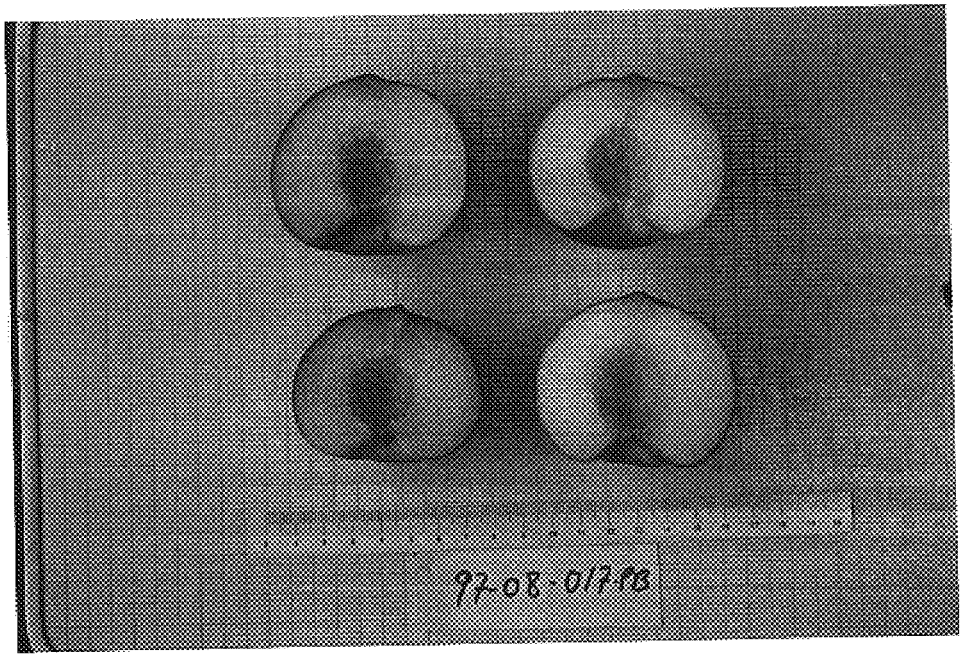
Figure 6:
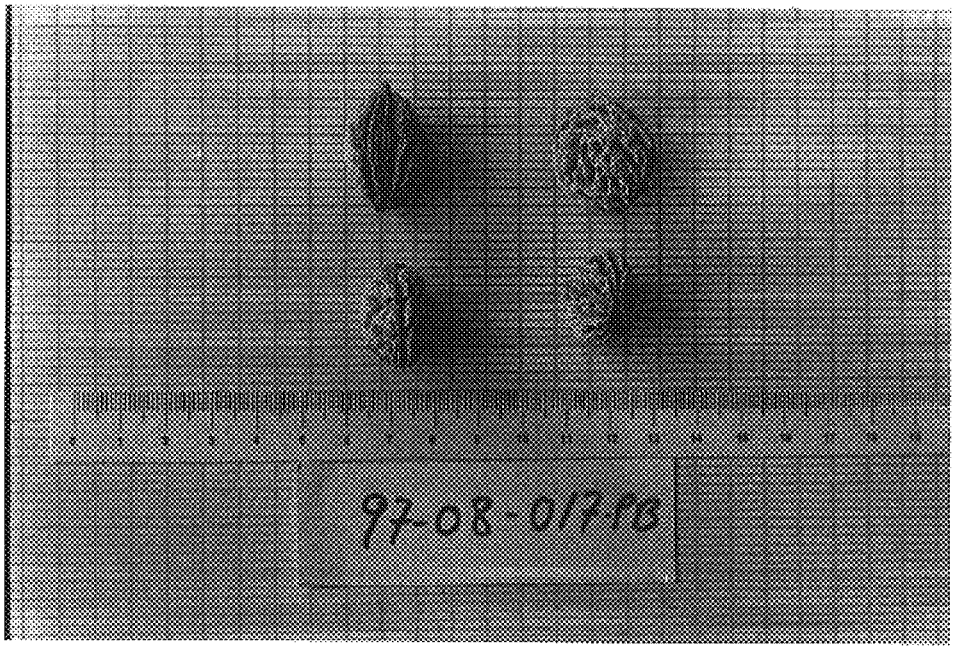

Typical branches (FIG. 1),

Branches with flowers (FIG. 2),

Several mature leaves showing both the dorsal and ventral coloration (FIG. 3), Several mature fruit showing their external coloration (FIG. 4), Several fruits of the subject variety are dissected in the equatorial plane to illustrate the flesh characteristics when the fruits are sufficiently matured for harvesting and shipment (FIG. 5), and Several typical stones (FIG. 6) of the new variety designated 97.08.017-PB; all in color as nearly true as it is reasonably possible to make in color illustrations of this character.

DETAILED DESCRIPTION OF THE NEW VARIETY

The following is a detailed description of the botanical and pomological characteristics of the subject peach. Color data are presented in The Royal Horticultural Society Colour Chart (R.H.S.C.C.) designations.

Where dimensions, sizes, colors and other characteristics are given, it is to be understood that such characteristics are approximations of averages set forth as accurately as practical.

The descriptions reported herein are from specimens grown at the orchard previously described, and which is located near the town of Cartaya (7° W., 37° N., 45 feet elevation), Huelva, Spain. Observations were made of the original seedling tree on its own root. Age of the observed plant.—About five years from planting in field.

Variety: 'PLAWHITE 5' Breeder Ref.: 97.08-017-PB.

*Classification.*—*Prunus persica* (L.) Bastch—Peach.

Tree:

*Size.*—Generally average to above average as compared to other common peach cultivars.

*Productivity.*—Approximately 22000 Kgrs/Ha.

*Form.*—The tree is considered upright to upright spreading in form.

*Height.*—The original seedling tree had approximately 3.00 m. at the end of the 2002 growing season.

*Width.*—The original seedling tree had approximately 2.70 m. at the end of the 2002 growing season.

*Current season growth.*—The current season growth for the new variety was approximately 0.9–1.0 m.

*Regularity of bearing.*—Regular.

Trunk:

*Thickness.*—Approximately 180 millimeters. In diameter when measured at a distance or approximately 15 cm. Above the soil level, at the end of the 2002 growing season.

*Bark texture.*—Considered moderately rough with numerous scarf skin and numerous flat oval lenticels being present.

*Bark coloration.*—Greyed-orange group (near 175C to 177D).

Branches:

*Size.*—Considered medium for the variety.

*Diameter.*—The branches have a diameter approximately of 80 millimeters. When measured during the 3rd year after grafting.

*Surface texture.*—Average, and appearing furrowed on wood which is several years old.

*Current season shoots.*—Surface texture, substantially glabrous.

*Color of mature branches.*—Greyed-orange group (near 175D to 177D).

*Current season shoots color.*—Greyed-orange group (near 175D to 175C).

Leaves:

*Size.*—Considered average for the species. Leaf measurements have been taken from vigorous upright current season growth at approximately midshoot.

*Leaf length.*—Approximately 155 to 180 millimeters.

*Leaf width.*—Approximately 44 to 50 millimeters.

*Leaf thickness.*—Approximately 1 to 2 millimeters.

*Leaf base shape.*—Slightly oblique.

*Leaf form.*—Lanceolate.

*Leaf tip form.*—Acuminate.

*Leaf color.*—Upperside — Yellow-green group (near 147A). Underside — Yellow-green group (near 147C to 148B).

*Leaf texture.*—Smooth.

*Leaf margins.*—Slightly crenate, considered generally uniform.

*Leaf petioles.*—Considered medium to long. Length — Approximately 10 to 12 millimeters. Diameter — Approximately 2 millimeters.

*Leaf glands.*—Type — Reniform. Size — Approximately 1 to 2 millimeters in length and 0.1 to 0.4 millimeters in width. Number — Generally more than 2 per side.

*Venation.*—Pinnately net veined.

*Mid-vein.*—Color RHS Yellow-green group (near 145D to 145C) when the leaves are young and reddish, Color RHS red group (near 45C to 46C) when the leaves are mature.

Flowers: Bloom occurs prior to vegetative bud break; solitary to occasional double individual flowers at a single node; perfect self-fertile.

*Blooming time.*—Considered very early in relation to other peach cultivars.

*Date of bloom.*—First, January 13. Full, January 30.

*Flower buds.*—Length — Approximately 7.5 millimeters. Diameter — Approximately 2.5 millimeters. Shape — Ovoid in form. Color — RHS Greyed-orange group (near 177B to 177A).

*Type.*—The new variety is considered to be a showy type flower.

*Flower diameter.*—At full bloom is approximately 43 to 47 millimeters.

*Bloom quantity.*—Very abundant.

*Pollen production.*—Fertile and abundant to allow a good fruit production.

*Petal size.*—Generally considered medium for the species. Length, approximately 18 to 20 millimeters. Width, approximately 16 to 19 millimeters.

*Petal shape.*—Rounded.

*Petal count.*—Nearly always 5.

*Petal texture.*—Smooth.

*Petal color.*—Red purple group (near 69D to 69C).

*Abaxial color of the petal.*—RHS Red-purple group (near 69D).

*Petal apex.*—The petal apices appear domed.

*Sepals.*—Length — Approximately 8 millimeters. Width — Approximately 5 millimeters. Number — Generally 5 per flower. Shape — Conical. Color — RHS Green group (near 139C to 138A).

*Flower pedicel.*—Length — Approximately 3 millimeters. Diameter — Approximately 2 millimeters. Color — RHS Yellow-green group (near to 144C).

Reproductive organs:

*Anthers.*—Length — Approximately 1.5 millimeters. Width — Approximately 1 millimeters. Color — RHS Greyed-orange group (near 169D to 169B).

*Pollen production.*—Pollen is abundant. Color — RHS Orange group (near 24B to 24A).

*Filaments.*—Length — Approximately 15 millimeters. Color RHS Red-purple group (near 69 D), and darkening with advanced maturity.

*Pistil.*—Length — Approximately 16 millimeters, including the ovary. Surface texture — Pubescent. Color — RHS Green group (near 138A).

Fruit:

*Maturity when described.*—The present variety of fruit is described, as it would be found in its firm ripe condition at full commercial maturity. In this regard, the first fruit of the present variety was picked on approximately April 15. The date of the last pick of the same fruit in that year was approximately April 25 in Cartaya (7° W., 37° N., 45 feet elevation), Huelva, Spain conditions.

*Size.*—Generally medium in size, and considered uniform. Average cheek diameter, approximately 63 to 65 millimeters. Average suture diameter, approximately 67 to 70 millimeters. Average axial diameter, approximately 73 to 75 millimeters.

*Fruit form.*—Slightly flat. Generally uniform.

*Fruit suture.*—Generally the suture appears as a very thin line, which extends from the base to the apex and which appears at same level of the skin.

*Stem cavity size.*—Considered medium for the species.

*Width.*—Approximately 20 to 21 millimeters.

*Length.*—Approximately 30 to 35 millimeters.

*Depth.*—Approximately 12 to 14 millimeters.

*Form.*—Considered ovoid.

*Fruit base.*—Generally concave rounded in form, and uniform.

*Fruit apex.*—Generally considered slightly depressed.

*Fruit skin.*—Generally considered average in thickness. Surface texture — The variety presents very light, short pubescence. Skin acidity — Considered neutral.

*Tenacious to flesh.*—Yes at commercial maturity.

*Tendency to crack.*—Not observed.

*Skin color.*—Generally 80% to 85% of the fruit surface covered with a red color RHS red group (near 47B to 47A).

*Skin ground color.*—Generally 15% to 20% of the fruit surface which has a yellow-green color group (near 149 D to 150 D)

*Firmness.*—3–4 Kg/cm$^2$ Firmness: It is the fruit's resistance to penetration measured in Kilograms (Kg/cm$^2$). The measure given has been obtained by the penetrometer ROZE Mod. Arbelette, with a 50 mm$^2$ section head.

*Flesh color.*—Generally RHS white group (near 155C to 155B).

*Flesh fibers.*—Present, numerous, very fine and red light colors. These fibers are present, at maturity, throughout the flesh.

*Flesh texture.*—Generally melting.

*Flavor.*—Considered sweet. Soluble solids, as °Brix, 10.

*Aroma.*—Pleasant and abundant.

*Eating quality.*—Generally considered very good to excellent and well above average when compared to other common commercial varieties.

Stone:

*Attachment.*—Generally the stone is considered to be a clingstone at full commercial maturity.

*Stone size.*—Generally considered medium for the species.

*Length.*—Approximately 27 to 28 millimeters.

*Width.*—Approximately 21 to 23 millimeters.

*Thickness.*—Approximately 17 to 19 millimeters.

*Stone form.*—Generally slightly oval.

*Stone color.*—Yellow-orange group (near 19 B to 20 B).

*Tendency to split.*—Slightly yes.

*Kernel.*—Form — ovoid. Length — approximately 13 to 14 millimeters. Width — approximately 8 to 10 millimeters.

*Market use.*—Fresh consumption in local market and long distance; not evaluated for other uses.

*Keeping quality.*—Fruit has stored well up to 15 days after harvest at temperatures of about 1° C.

Winter hardiness and drought/heat tolerance: No winter injury has been noted during the several years of evaluation in the South of Spain. The current variety has not been intentionally subjected to drought or heat stress and therefore this information is not available.

Resistance to insects and disease: No particular susceptibilities were noted.

Shipping quality: Well above average.

Although this new variety of peach tree possesses the described characteristics noted above, as a result of the growing conditions prevailing in Cartaya (7° W., 37° N., 45 feet elevation), Huelva, Spain, it is to be expected that variations in these characteristics may occur when farmed in areas with different climatic conditions, different soil types, and/or varying cultural practices.

I claim:

1. A new and distinct variety of peach tree substantially as illustrated and described, characterized by its low chilling requirements, its very early ripening, attractive fruit shape and color, clingstone fruit, white flesh, medium firm fruit, and good fruit quality.

* * * * *